United States Patent [19]

Köhler et al.

[11] Patent Number: 4,740,624

[45] Date of Patent: Apr. 26, 1988

[54] PROCESS FOR THE PREPARATION OF KETONES

[75] Inventors: Manfred Köhler, Darmstadt; Michael Römer, Rodgau; Claus P. Herz, Heidelberg, all of Fed. Rep. of Germany

[73] Assignee: Merck Patent Gesellschaft mit beschrankter Haftung, Darmstadt, Fed. Rep. of Germany

[21] Appl. No.: 848,546

[22] Filed: Apr. 7, 1986

[30] Foreign Application Priority Data

Apr. 6, 1985 [DE] Fed. Rep. of Germany ....... 3512541

[51] Int. Cl.$^4$ .............................................. C07C 45/64
[52] U.S. Cl. ................................. 568/316; 568/315; 568/312; 568/43; 558/415
[58] Field of Search ................. 568/316, 318, 315, 43, 568/312; 558/415

[56] References Cited

U.S. PATENT DOCUMENTS 3,953,494  4/1976  Meyers et al. ..................... 568/322

FOREIGN PATENT DOCUMENTS 0094347 11/1983 European Pat. Off. ............ 568/318

OTHER PUBLICATIONS

Meyers et al, J. Org. Chem., vol. 43, pp. 1985–1990 (1978).
Lauritzen et al, Acta Chemica Scan, vol. 35, pp. 263–268 (1981).
Makosza et al, J. Org. Chem., vol. 50, pp. 3722–3727 (1985).
Meyers et al, J.A.C.S., vol. 91, pp. 7510–7512 (1969).

*Primary Examiner*—James H. Reamer
*Attorney, Agent, or Firm*—Millen & White

[57] ABSTRACT

Ketones of the formula II

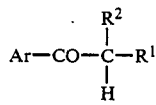

with Ar, $R^1$ and $R^2$ as indicated below, can be hydroxylated, readily and in high yields, in the α-position using tetrahalogenomethanes and alkali metal hydroxides under phase-transfer conditions.

17 Claims, No Drawings

PROCESS FOR THE PREPARATION OF KETONES

BACKGROUND OF THE INVENTION

This invention relates to a process for the preparation of α-hydroxylated ketones from ketones using a tetrahalogenomethane and alkali metal hydroxide under phase-transfer conditions.

The α-Hydroxylated ketones preparable by the process of this invention are useful as initiators for the photopolymerization of unsaturated compounds, as described in, for example, German Patent Specification No. 2,722,264. All the products of this invention can be used in accordance with that disclosure and its U.S. equivalents U.S. Pat. Nos. 4,347,111 and 4,477,681, which disclosures are incorporated by reference herein.

A number of processes for the preparation of α-hydroxylated ketones has been disclosed. A review can be found in Houben-Weyl, Methoden der Organischen Chemie (Methods of Organic Chemistry) published by George Thieme, Stuttgart, vol. VII/2c and in the abovementioned patent specification.

The processes hitherto disclosed have a number of disadvantages. Thus, for example, using chlorine or bromine, ketones of the formula II are converted into the corresponding α-halogeno ketones. The latter can be reacted with metal alcoholates to give α-alkoxy epoxides, whose hydrolysis provides the desired α-hydroxylated ketones of the formula I. However, the resulting wide variety of by-products reduces the yield of desired product.

Under basic conditions α-halogeno ketones can be hydrolyzed directly to α-hydroxylated ketones. The latter often suffer base-catalyzed isomerizations or Favorsky rearrangements. The resultant by-products likewise lead to reductions in yield and decreases in the quality of the products of the process.

A process for the preparation of α-hydroxylated ketones is disclosed in European Published Specification No. 094,347. α-halogeno ketones are reacted with compounds which generate hydroxide ions in the presence of a phase-transfer catalyst. The requisite halogeno ketones must previously be prepared in an additional process step from the ketones of the formula II. In addition to an increase in the work and costs expended, because substituents on the starting compounds are intolerant of the reaction conditions, the preparation of the α-halogeno ketones is, frequently associated with by-product formation and the reduction in yield resulting from this.

V. M. Kolb, in a dissertation at Southern Illinois University, Carbondale, 1976, describes a process for the direct α-hydroxylation of ketones by reaction with carbon tetrachloride and powdered potassium hydroxide in tert-butanol as solvent. In addition to providing yields which mostly are only moderate, hydroxy ketones of the formula I readily suffer rearrangement under the reaction conditions described. Thus, 3,3,6,6-tetramethyl-1,4-diphenyl-2,5,7-trioxabicyclo-[2.2.1]heptane, formed via the intermediate cis-2,2,5,5-tetramethyl-3,6- dihydroxy- 3,6-diphenyl-1,4-dioxane with elimination of water, is isolated in place of 1-phenyl-2-hydroxy-2-methyl-1-propanone. An additional disadvantage is the necessary restriction to the use of powdered, and thus costly and difficult-to-handle, potassium hydroxide as the compound generating hydroxide ions.

SUMMARY OF THE INVENTION

Thus, it is an object of this invention to provide a process which permits the preparation of α-hydroxylated ketones of the formula I from ketones of the formula II without additional intermediates, in high yields, without by-product formation, in stable form, and using reasonably priced auxiliaries.

Upon further study of the specification and appended claims, further objects and advantages of this invention will become apparent to those skilled in the art.

These objects have been achieved by providing the process according to this invention for the preparation of ketones.

Thus, this invention relates to a process for the preparation of ketones of formula I

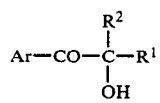

in which Ar is aryl of 6–14 C atoms or such an aryl group which is substituted by $C_1$–$C_{12}$ alkyl, $C_1$–$C_4$ alkoxy, $C_1$–$C_4$ alkylthio, Cl, Br or CN, $R^1$ and $R^2$ are identical or different and each is $C_1$–$C_7$ alkyl, $C_3$–$C_8$ cycloalkyl or, together with the C atom to which they are bonded, form $C_3$–$C_9$ cycloalkyl, wherein a ketone of the formula II

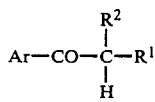

with the abovementioned meanings for Ar, $R^1$ and $R^2$, is reacted with a tetrahalogenomethane of formula III

in which b and c independently are 0–4, a is 0–2, and $a+b+c=4$, and an alkali metal hydroxide under phase-transfer conditions.

DETAILED DISCUSSION

The reaction is carried out in a straightforward manner. The ketones of the formula II which are to be used as starting materials are known or can be prepared by methods known per se, as are described in the literature (for example in standard works such as Houben-Weyl, Methoden der Organischen Chemie, published by Georg Thieme, Stuttgart, vol. VII), specifically under reaction conditions as are known and suitable for the reactions mentioned. It is also possible to make use of variants which are known per se but are not mentioned here in detail.

In the ketones of the formula II which are to be hydroxylated, Ar is preferably phenyl or substituted phenyl, in particular phenyl, 4-methylphenyl, 4-ethylphenyl, 4-isopropylphenyl, 4-dodecylphenyl, 3,4-dimethylphenyl, 4-methoxyphenyl or 4-chlorophenyl. $R^1$ and $R^2$ are preferably $C_1$–$C_4$ alkyl, $C_3$–$C_6$ cycloalkyl or, together with the C atom to which they are bonded, are $C_3$–$C_6$ cycloalkyl, in particular methyl, ethyl, propyl, butyl or cyclohexyl or, together with the C atom to which they are bonded, cyclohexyl. Ar is further 1-naphthyl, 2-naphthyl, 1-anthracenyl, 2-anthracenyl, 5-anthracenyl, 1-phenanthryl, 2-phenanthryl or 9-phenanthryl.

In the tetrahalogenomethanes of the formula III, a is preferably O, in particular a=c=0, b=4, or a=b=0, c=4; carbon tetrachloride is very particularly preferred.

Suitable alkali metal hydroxides are the hydroxides of lithium, sodium, potassium, rubidium and cesium, preferably those of sodium and potassium, in particular sodium hydroxide. Two-phase reactions with a solid-liquid phase transition normally require, to achieve acceptable reaction rates, the largest possible surface area of the solid phase. For example, according to U.S. Pat. No. 3,830,862, the elimination of dibenzyl sulfone in the system potassium hydroxide/carbon tetrachloride takes place only with finely powdered potassium hydroxide and not with commercially available pellets. Thus, it was all the more surprising that very goods results are achieved even with the alkali metal hydroxides in the form of pellets, granules or flakes, which are considerably easier to handle. It is furthermore possible for the alkali metal hydroxides also to be powdered or applied to solid supports. "By phase-transfer conditions" herein is meant that an effective amount of phase-transfer agent is also utilized during the reaction.

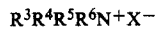

$$R^3R^4R^5R^6N^+X^- \quad\quad IV$$

The compounds used as phase-transfer reagents are selected from the groups of quaternary ammonium compounds, of oligoethylene or polyethylene glycols or their monoethers or bisethers, or of cyclic polyethylene glycol ethers ("crown ethers").

The radicals $R^3$, $R^4$, $R^5$ and $R^6$ in the quaternary ammonium compounds of the formula IV are identical or different and are benzyl or straight-chain or branched alkyl having a total of 4 to 30 C atoms. X is a suitable anion such as, for example F, Cl, CN, OH, $HSO_4$ or $CH_3OSO_3$. The choice of the anion is not crucial; it is possible to use all singly or multiply charged anions. Benzyltrimethylammonium hydrogen sulphate and methyltrioctylammonium chloride are particularly preferred. It is possible, where appropriate, for the quaternary ammonium compounds of the formula IV also to be immobilized by chemical bonding onto a liquid or solid polymeric support.

A preferred group of phase-transfer reagents is the oligoethylene and polyethylene glycols and their monoethers or bisethers, which correspond to the general formula $R^7O-(CH_2-CH_2O-)R^8$ in which n is equal to or larger than 2, and $R^7$ and $R^8$ are identical or different, and are alkyl, aryl and/or cycloalkyl groups.

$R^7$ and/or $R^8$ can be H and/or branched and unbranched alkyl radicals, having 1 to 20, preferably 1 to 10, C atoms, cycloalkyl radicals having 3 to 15, preferably having 5 to 10, C atoms, and/or aryl radicals having 6 to 14, preferably having 6 to 10, C atoms, in particular phenyl and substituted phenyl.

It is possible to use as solvents both homogeneous compounds such as, for example, hexaethylene glycol monomethyl and dimethyl ether, octaethylene glycol monoethyl and diethyl ether and decaethylene glycol monodecyl and didecyl ether, and mixtures of ethers with various degrees of oligomerization and corresponding mean molecular weights, such as, for example, polyethylene glycol monomethyl and dimethyl ether (n=7.9; mean molecular weight 400) and polyethylene glycol monomethyl and dimethyl ether (n=22.3; mean molecular weight 1,000).

Aromatic oligoethylene glycol monoethers are particularly advantageous, in particular decaethylene glycol monoaryl ethers and substituted decaethylene glycol monoaryl ethers. A particularly suitable compound is decaethylene glycol mono(4-nonylphenyl) ether, which thus represents a preferred phase-transfer reagent in the process according to the invention for the preparation of ketones.

The molar ratio of tetrahalogenomethane and alkali metal hydroxide, relative to the ketone of the formula II used as substrate, is in each case at least 1:1, preferably 1 to 2:1.

The amount of phase-transfer reagent can be chosen as desired within wide limits, preferably being 10 to 100% by weight relative to ketone used.

The reaction is carried out by mixing the components, ketone of the formula II, tetrahalogenomethane of the formula III and alkali metal hydroxide, and by heating the stirred reaction mixture to the temperature required for the reaction, it possibly being advantageous, however, to add the alkali metal hydroxide slowly to the other components which have already been introduced. The reaction temperatures are normally 0° to 100°, preferably 10° to 50°. The reaction times are 1 to 60 hours, preferably 12 to 48 hours.

The use of ultrasound as described by, for example, Lucke and Damiano, J. Amer. Chem. Soc. 102 (1980) 7926 for the Grignard reaction may have an advantageous effect on the reaction. Agitating the reaction mixture by e.g. shaking or stirring is generally useful in performing the reaction.

It is possible to add to the reaction mixture another inert organic solvent to decrease the viscosity of the reaction mixture, to decrease the reactivity of especially reactive components or to reduce the amount of phase-transfer reagent. The amount of solvent and co-solvent can be varied within wide limits, preferably 0.5 to 50 times the amount of starting material ketone. The ratio of solvent and co-solvent is not critical, preferably being 1 : 10 to 10 : 1.

Preferred inert solvents are those which are stable under the reaction conditions chosen, such as, for example, aliphatic or aromatic hydrocarbons, in particular tetrahydrofuran or dioxane. It is also possible to add mixtures of these solvents.

For working up after the reaction has been carried out, water is preferably added to the reaction mixture, and the desired product is isolated by extraction followed by distillation, chromatography or crystallization.

The ketones used can in this manner be straightforwardly α-hydroxylated in high yields. The residue from working up, which consists mainly of unchanged phase-transfer reagent, can, if it displays unchanged reactivity, be reused for another reaction batch.

In a particularly preferred embodiment of the invention, 1-phenyl-2-hydroxy-2-methyl-1-propanone, 1-(4-isopropylphenyl)-2-hydroxy-2-methyl-1-propanone and 1-hydroxycyclohexyl phenyl ketone are prepared, as initiators for the photopolymerization of unsaturated compounds, from 1-phenyl-2-methyl-1-propanone, 1-(4-isopropylphenyl)-2-methyl-1-propanone or cyclohexyl phenyl ketone using carbon tetrachloride, sodium hydroxide and decaethylene glycol mono(4-nonylphenyl) ether, where appropriate with the addition of an inert solvent.

Thus, the present invention has made available a very advantageous process for the preparation of α-hydroxylated ketones which is straightforward and takes place with high yields.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

A total of 552 g of sodium hydroxide is added in portions, within 48 hours, to a stirred mixture of 895 g of 1-phenyl-2-methyl-1-propanone, 900 ml of carbon tetrachloride, 1.8 l of toluene and 300 ml of decaethylene glycol mono(4-nonylphenyl) ether at 15°.

For the working up, 3 l of toluene is added, and the mixture is extracted by stirring with 1.8 l of water. The organic phase is separated off, and the solvent is removed under reduced pressure. The residue is subjected to fractional distillation. After a small fore-run, 877 g (89% of theory) of virtually colorless 1-phenyl-2-hydroxy-2-methyl-1-propanone, which has a purity of 98.5% determined by gas chromatography, distills over at 50 to 100 Pa and 75°–85° C.

The residue from the distillation, which contains the phase-transfer reagent, can be reused with unchanged activity in another reaction batch.

EXAMPLE 2

A total of 44 g of sodium hydroxide in the form of pellets is added, within 40 hours, to a stirred mixture of 74.5 g of 1-phenyl-2-methyl-1-propanone, 75 ml of carbon tetrachloride, 150 ml of toluene and 1 g of dibenzo-18-crown-6 (dibenzo[b,k]- 1,4,7,10,13,16-hexaoxacyclooctadecadiene) at 15°.

The working up is carried out in analogy to Example 1 and, after distillation, 65.3 g (78% of theory) of pure 1-phenyl-2-hydroxy-2-methyl-1-propanone are obtained.

EXAMPLE 3

A total of 44 g of granulated sodium hydroxide is introduced, within 20 hours, into a stirred mixture of 74.5 g of 1-phenyl-2-methyl-1-propanone, 75 ml of carbon tetrachloride, 150 ml of toluene and 25 ml of methyltrioctylammonium chloride at 15°.

After working up as described in Example 1 and purification by distillation, 62.1 g (74% of theory) of pure 1-phenyl-2-hydroxy-2-methyl-1-propanone are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a stable α-hydroxylated ketone of the formula,

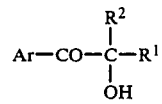

in which Ar is aryl of 6–14 C atoms or aryl of 6–14 C atoms which is substituted by $C_1$–$C_{12}$ alkyl, $C_1$–$C_4$ alkoxy, $C_1$–$C_4$ alkylthio, Cl, Br or CN, $R^1$ and $R^2$ are identical or different and each is $C_1$–$C_7$ alkyl, $C_3$–$C_8$ cycloalkyl or, together with the connecting C atoms form $C_3$–$C_9$ cycloalkyl, comprising reacting effective amounts of a ketone of the formula

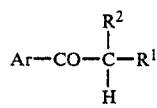

wherein Ar, $R^1$ and $R^2$ are as defined above, with a tetrahalogenomethane of the formula

in which b and c independently are 0–4, a is 0–2, and $a+b+c=4$, and solid alkali metal hydroxide, whereby a liquid-solid two phase system is formed, the reaction being carried out under liquid-solid phase-transfer conditions in the presence of a phase-transfer agent. which is an oligoethylene or polyethylene glycol, a monoether or bisether thereof, a cyclic polyethylene glycol ether, a quaternary ammonium compound of the general formula

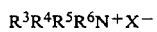

in which $R^3$, $R^4$, $R^5$ and $R^6$ are identical or different and each is alkyl or benzyl, all four groups together having 4 to 30 C atoms, and X is a singly or multiply charged compatible anion, or a mixture thereof.

2. A process of claim 1, wherein $a=c=0$ and $b=4$.

3. A process of claim 1 wherein sodium hydroxide is the alkali metal hydroxide.

4. A process of claim 3, wherein a decaethylene glycol monoaryl ether is used as phase-transfer reagent.

5. A process of claim 3, wherein benzyltrimethylammonium hydroxide, tetrabutylammonium chloride, butyltriethylammonium hydrogen sulphate or methyltrioctylammonium chloride is used as phase-transfer reagent.

6. A process of claim 3, wherein said quaternary ammonium compound used as phase-transfer reagent is bonded to a polymeric support.

7. A process of claim 5, wherein said quaternary ammonium compound used as phase-transfer reagent is bonded to a polymeric support.

8. A process of claim 3, wherein $a=c=0$ and $b=4$.

9. A process of claim 8, wherein benzyltrimethylammonium hydroxide, tetrabutylammonium chloride, butyltriethylammonium hydrogen sulphate or methyltrioctylammonium chloride is used as phase-transfer reagent.

10. A process of claim 1 wherein 1-phenyl-2-hydroxy-2-methyl-1-propanone, 1-(4-isopropylphenyl)-2-hydroxy-2-methyl-1-propanone or 1-hydroxycyclohexyl phenyl ketone is prepared by utilizing the corresponding ketone 1-phenyl-2-methyl-1-propanone, 1-(4-isopropylphenyl)-2-methyl-1-propanone or cyclohexyl phenyl ketone in said process.

11. A process of claim 9 wherein 1-phenyl-2-hydroxy-2-methyl-1-propanone, 1-(4-isopropylphenyl)-2-hydroxy-2-methyl-1-propanone or 1-hydroxycyclohexyl phenyl ketone is prepared by utilizing the corresponding ketone 1-phenyl-2-methyl-1-propanone, 1-(4-isopropylphenyl)-2-methyl-1-propanone or cyclohexyl phenyl ketone in said process.

12. A process of claim 1 carried out in the presence of a solvent which is an oligoethylene glycol monoether.

13. A process of claim 1 wherein the mole ratios of hydroxide and tetrahalogenomethane to starting ketone, independently, are at least 1:1.

14. A process of claim 11 wherein the amount of phase-transfer agent is 10–100% by weight based on starting ketone.

15. A process of claim 1 carried out at a temperature of 0°–100° C.

16. A process of claim 1, wherein said phase-transfer agent is recovered for reuse.

17. A process of claim 1, wherein the alkali metal hydroxide is present in the form of pellets, granules or flakes.

* * * * *